United States Patent
Iida et al.

(10) Patent No.: US 6,946,559 B2
(45) Date of Patent: Sep. 20, 2005

(54) METHOD OF CONVERTING FUNCTIONAL GROUP THROUGH HALOGEN-METAL EXCHANGE REACTION

(75) Inventors: Takehiko Iida, Aichi (JP); Toshihiro Wada, Aichi (JP); Toshiaki Mase, Okazaki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 200 days.

(21) Appl. No.: 10/182,622

(22) PCT Filed: Jan. 24, 2001

(86) PCT No.: PCT/JP01/00463

§ 371 (c)(1),
(2), (4) Date: Sep. 5, 2002

(87) PCT Pub. No.: WO01/57046

PCT Pub. Date: Aug. 9, 2001

(65) Prior Publication Data

US 2003/0130511 A1 Jul. 10, 2003

(30) Foreign Application Priority Data

Feb. 2, 2000 (JP) ........................................ 2000-024613

(51) Int. Cl.[7] .......................... C07D 213/74; C07C 47/55
(52) U.S. Cl. ....................... 546/314; 570/101; 570/260
(58) Field of Search ...................... 570/101.25; 546/314

(56) References Cited

U.S. PATENT DOCUMENTS 3,972,953 A * 8/1976 Lyons ......................... 570/191

FOREIGN PATENT DOCUMENTS

JP  56-112916  9/1981
JP  10-130179  5/1998

OTHER PUBLICATIONS

Kitagawa Kazuya et al., "Halogen–Magnesium Exchange Via Trialkylmagnesates for the Preparation of Aryl– and Alkenylmagnesium Reagents", Angew. Chem. Int. Ed., 2000, vol. 39, No. 14, pp. 2481–2483.

* cited by examiner

*Primary Examiner*—Zinna Northington Davis
(74) *Attorney, Agent, or Firm*—Wenderoth, Lind & Ponack, L.L.P.

(57) ABSTRACT

A method by which a halogen atom of a halogen compound can be efficiently replaced with an electrophilic group.

Also provided are: a reagent for converting a functional group through a halogen-metal exchange reaction, characterized by comprising either a mixture of a magnesium compound represented by the formula $R^1$—Mg—$X^1$ (I) (wherein $R^1$ represents a halogen atom or an optionally substituted hydrocarbon residue; and $X^1$ represents a halogen atom) and an organolithium compound represented by the formula $R^2$—Li (II) (wherein $R^2$ represents an optionally substituted hydrocarbon residue) or a product of the reaction of the magnesium compound with the organolithium compound; and a process for producing with the reagent a compound in which a halogen atom of a halogen compound has been replaced with an electrophilic group.

11 Claims, No Drawings

METHOD OF CONVERTING FUNCTIONAL GROUP THROUGH HALOGEN-METAL EXCHANGE REACTION

This application is a 371 of PCT/JP01/00463 filed Jan. 24, 2001.

TECHNICAL FIELD

This invention is useful in the field of chemical industry. More particularly, the present invention relates to a process for exchanging functional groups and to a reagent for halogen-metal exchange reaction, with industrial advantage, for a variety of useful compounds in the fields of chemical industry products, agrochemicals, and pharmaceuticals.

BACKGROUND ART

Halogen-metal exchange reaction is widely used as a technique for substituting a halogen atom present in a halogenated organic compound into other substituent. As a reagent employed in the halogen-metal exchange reaction are exemplified Grignard reagents and organolithium reagents.

Since Grignard reagents have low reactivity in general, it is necessary to often use such reagents in an excess when reacted with an aryl chloride or an aryl bromide. Also, such reagents require a long reaction time. Therefore, reaction with the Grignard reagents is of no practical use from standpoint of industrial production (see Tetrahedron Letters, Vol. 40, pages. 4339–4342 (1999) by F. Trecourt, et al.) On the other hand, the Grignard reagents have a high reactivity for practical use to an aryl iodide, but it is troublesome to introduce an iodine atom in the way of synthetic route. The reaction using such Grignard reagents is, therefore, not desirable in view of industrial production (see Journal of Organic Chemistry, Vol. 57, pages 407–410 (1992) by Hisao Nishiyama, et al., Tetrahedron Letters Vol. 28, No. 47, pages 5845–5848 (1987) by Naomichi Furukawa, et al., and Journal of Organic Chemistry, Vol. 56, pages 5739–5740 (1991) by Richard M. Turner, et al.).

Organolithium reagents are widely used in halogen-metal exchange reaction, and can be also applied to a wide range of reaction substrates. However, thermostability of such organolithium compound itself or that of an intermediate lithio compound by-produced is generally not high. It is, therefore, essential to often carry out the reaction under the conditions of extreme low temperature which is unsuitable for industrial production (see. Journal of Medicinal Chemistry, Vol. 42, pages 1088–1099, (1999) by Tatsuzo Ukita, et al., Tetrahedron Letters, Vol. 37, No. 15, pages 2537–2540 (1996) by Dongwei Cai, et al., and Journal of Organic Chemistry, Vol. 58, pages 4382–4388 (1993) by Jun'ichi Uenishi et al.).

Further, exchange reactions of functional groups in iodo alkenes (see Journal of Organic Chemistry, Vol. 64, pages 1080–1081 (1999) by Mario Rottlander, et al.) and in bromoaryl compounds or bromoheteroaryl compounds (see Tetrahedron letters, Vol. 40, pages 7449–7453 (1999) by Mohamed Abarbri, et al.), using diisopropylmagnesium, are also known.

DISCLOSURE OF INVENTION

In the known methods as mentioned above, there is, however, restriction in the reaction conditions which are unsuitable for industrial production, e.g. extreme low temperature and a narrow range of reaction substrates to be applied. Such drawbacks are required to be overcome. It is, therefore, an object of the present invention to provide a process for exchanging functional groups, which is applicable to industrial production of various useful compounds in a wide range of fields such as chemical industry products, agrochemicals or pharmaceuticals.

The present inventors have found that, as a result of diligent studies of exchanging halogen atoms in organic compounds for electrophilic groups, a halogen atom can be substituted with an electrophilic group in high yield at a low temperature of about 0° C. The substitution is carried out by reacting a halogen atom attached to a carbon atom of a double bond or attached to a carbon atom adjacent to the carbon atom of the triple bond in an organic compound having at least one carbon-carbon double or triple bond, with a reaction product between a magnesium compound and an alkali metal compound, and reacting the resultant product with a compound having an electrophilic group, followed by optional treatment with an acid. It has also been found that said exchange of the halogen atom and said exchange reagent can be very widely used in the field of industry. The present invention has been completed on the basis of these findings.

Namely, the present invention relates to an industrially useful reagent for exchanging halogen atoms for functional groups by halogen-metal exchange reaction, wherein the reagent contains a mixture of a magnesium compound and an organolithium compound, or contains a reaction product thereof. The present invention is also directed to a process for substituting a halogen atom in a halogenated compound with an electrophilic group by use of said reagent. More particularly, the present invention relates to (1) an exchange reagent for a functional group by halogen-metal exchange reaction, which comprises a mixture of
(A) (1) a magnesium compound represented by the formula:

$$R^1\text{—Mg—}X^1 \quad (I)$$

(wherein $R^1$ is a halogen atom or an optionally substituted hydrocarbon residue, and $X^1$ is a halogen atom) or (2) a member selected from the group consisting of diethylmagnesium, dipropylmagnesium, diisopropylmagnesium, di-n-butylmagnesium, di-sec-butylmagnesium, di-tert-butylmagnesium, diphenylmagnesium, divinylmagnesium, diallylmagnesium, di(2-furyl)magnesium, di(3-furyl)magnesium, di(2-thienyl)magnesium, di(3-thienyl)magnesium and dibenzylmagnesium and (B) an organolithium compound represented by the formula:

$$R^2\text{—Li} \quad (II)$$

(wherein $R^2$ is an optionally substituted hydrocarbon residue) or a reaction product from (I) and (II).

(2) the exchange reagent as described above in the item (1), wherein the reaction product is
a compound of the formula III:

$$(R^a R^b R^c Mg)^-.Li^+ \quad (III)$$

(wherein $R^a$, $R^b$ and $R^c$ are same or differently an optionally substituted hydrocarbon residue), or
a compound of the formula IV:

$$(R^d R^e R^f R^g Mg)^{2-}.2Li^+ \quad (IV)$$

(wherein $R^d$, $R^e$, $R^f$ and $R^g$ are same or differently an optionally substituted hydrocarbon residue).

(3) the exchange reagent as described above in the item (2), wherein $R^a$, $R^b$ and $R^c$ are each n-butyl.

(4) the exchange reagent as described in the item (2), wherein $R^d$, $R^e$, $R^f$ and $R^g$ are each n-butyl.

(5) an exchange process for exchanging a halogen atom present in a halogenated compound for an electrophilic group, which comprises reacting (i) a halogenated compound having in the molecule at least one halogen atom or one double or triple bond to which is attached a halogen-substituted carbon atom, with (ii) an exchange reagent as described above in the item (1) or (2), reacting the resultant product with (iii) a compound having an electrophilic group, and optionally treating the resultant product with an acid.

(6) the exchange process as described above in the item (5), wherein the halogenated compound is a compound represented by the formula V:

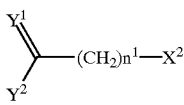
(V)

(wherein $Y^1$ is a divalent organic residue, $Y^2$ is a monovalent organic residue, or $Y^1$ and $Y^2$, when taken together, represent a trivalent organic residue, $X^2$ is a halogen atom, and $n^1$ is 0 or 1) or a compound represented by the formula VI:

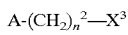
(VI)

(wherein A is an optionally substituted aromatic ring, $n^2$ is 0 or 1, and $X^3$ is a halogen atom).

(7) the exchange process as described above in the item (5), wherein the halogenated compound is

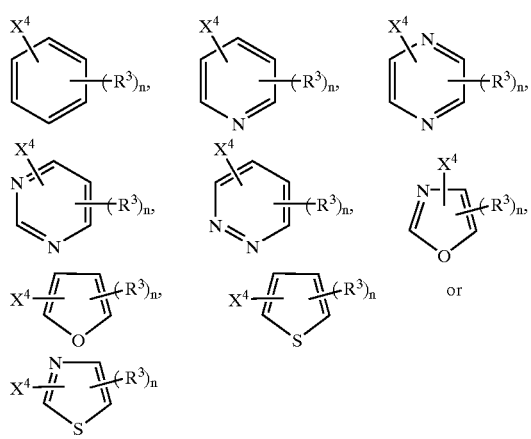
(VII)

(wherein $X^4$ is a halogen atom, $R^3$ is a hydrogen atom, a protected amino group, an optionally substituted hydrocarbon group, an optionally substituted hydrocarbon-oxy group or a halogen atom, and n is 1 or 2).

(8) the exchange process as described above in the item (5), wherein the halogenated compound is a compound represented by the formula VIII:

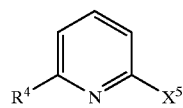
(VIII)

(wherein $R^4$ is a hydrogen atom, a protected amino group, an optionally substituted hydrocarbon group, an optionally substituted hydrocarbon-oxy group or a halogen atom, and $X^5$ is a halogen atom).

(9) the exchange process as described above in the item (5), wherein the compound having an electrophilic group is benzaldehyde, chlorotrimethylsilane, or N,N-dimethylformamide.

(10) the exchange process as described above in the item (5), wherein the exchange reagent is an exchange reagent as described above in the item (1), the magnesium compound represented by the formula (I) as described above in the item (1) is n-butylmagnesium bromide or n-butylmagnesium chloride, and the organolithium compound represented by the formula (II) is n-butyllithium.

(11) the exchange process as described above in the item (5), wherein the reagent is an exchange reagent as described above in the item(2), the compound represented by the formula (III) as described above in the item (2) is tri-n-butylmagnesium lithium, and the compound represented by the formula (IV) as described above in the item (2) is tetra-n-butylmagnesium dilithium.

(12) a mixture of (A) (1) a magnesium compound represented by the formula:

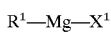
(I)

(wherein $R^1$ is an optionally substituted hydrocarbon residue and $X^1$ is a halogen atom) or (2) a member selected from the group consisting of diethylmagnesium, dipropylmagnesium, diisopropylmagnesium, di-n-butylmagnesium, di-sec-butylmagnesium, di-tert-butylmagnesium, diphenylmagnesium, divinylmagnesium, diallylmagnesium, di(2-furyl)magnesium, di(3-furyl)magnesium, di(2-thienyl)magnesium, di(3-thienyl)magnesium and dibenzylmagnesium and (B) an organolithium compound represented by the formula:

(II)

(wherein $R^2$ is an optionally substituted hydrocarbon residue).

(13) a process for preparing a compound wherein a halogen atom present in a halogenated compound is substituted with an electrophilic group, which comprises reacting (i) a halogenated compound having in the molecule at least one halogen atom or one double or triple bond to which is attached a halogen-substituted carbon atom, with (ii) an exchange reagent as described above in the item (1) or (2), reacting the resultant product with (iii) a compound having an electrophilic group, and optionally treating the resultant product with an acid, and

(14) the exchange process as described above in the item (12) for preparing 6-bromo-2-formylpyridine or a compound represented by the formula:

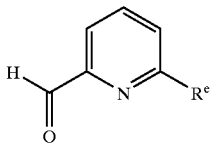

(wherein $R^e$ is a protected amino group), which comprises reacting 2,6-dibromopyridine or a compound represented by the formula:

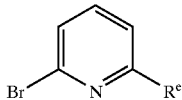

(wherein $R^e$ is a protected amino group), with a mixture of n-butyl magnesium chloride and n-butyllithium or a reaction product thereof, reacting the resultant product with N,N-dimethylformamide and treating the resultant product with an acid.

The present reagent used for exchange reaction contains a mixture of a magnesium compound (I) represented by the formula:

$$R^1\text{—}Mg\text{—}X^1 \quad (I)$$

(wherein $R^1$ is a halogen atom or an optionally substituted hydrocarbon residue, and $X^1$ is a halogen atom) and an organolithium compound (II) represented by the formula:

$$R^2\text{—}Li \quad (II)$$

(wherein $R^2$ is an optionally substituted hydrocarbon residue), or contains a reaction product obtained from (I) and (II).

The halogen atoms represented by $R^1$ and $X^1$ in the above formulae include, for example, chlorine, bromine, fluorine or iodine, among which chlorine, bromine or iodine is preferable, and chlorine or bromine is more preferable.

The hydrocarbon residues represented by $R^1$ and $R^2$ for optionally substituted hydrocarbon groups include, for example, linear or branched aliphatic hydrocarbon groups and cyclic hydrocarbon groups, having carbon atoms of 1 to 20. More specifically, examples of said groups are alkyl, alkenyl, alkynyl, cycloalkyl, aryl, aralkyl or the like.

The alkyl groups include, for example, straight or branched $C_{1-12}$ alkyl groups such as methyl, ethyl, propyl, isopropyl, butyl, isobutyl, pentyl, hexyl, heptyl, octyl, nonyl, decyl, undecyl, dodecyl or the like, among which $C_{1-6}$ alkyl such as methyl, ethyl, propyl, isopropyl, butyl, isobutyl, sec-butyl, tert-butyl, or pentyl are preferable.

The alkenyl groups include, for example, $C_{2-6}$ alkenyl such as vinyl, allyl, isopropenyl, butenyl, isobutenyl, sec-butenyl or the like, among which $C_{2-4}$ alkenyl such as vinyl, allyl, and isopropenyl are preferable.

The alkynyl groups include, for example, $C_{2-6}$ alkynyl such as propargyl, ethynyl, butynyl, 1-hexynyl or the like, among which propargyl, ethynyl or butynyl is preferable.

The cycloalkyl groups include, for example, $C_{3-6}$ cycloalkyl such as cyclopropyl, cyclobutyl, cyclopentyl, cyclohexyl or the like, which may be fused or condensed with a benzene ring optionally substituted with 1 to 3 lower alkoxy groups (e.g. $C_{1-6}$ alkoxy such as methoxy and the like)

The aryl groups include, for example, $C_{6-14}$ aryl such as phenyl, biphenylyl, naphthyl (e.g. 1-naphthyl or 2-naphthyl), indenyl (e.g. 1-indenyl or 2-indenyl), anthlyl (e.g. 1-anthlyl, 2-anthlyl or 3-anthlyl), phenanthlyl (e.g. 1-phenanthlyl, 2-phenanthlyl, 3-phenanthyl, 4-phenanthlyl or 9-phenanthlyl), among which $C_{6-10}$ aryl such as phenyl, 1-naphthyl or 2-naphthyl is more preferable.

The aralkyl groups include, for example, $C_{7-15}$ aralkyl such as benzyl, phenethyl, diphenylmethyl, 1-naphthylmethyl, 2-naphthylmethyl, 2-phenylethyl, 2,2-diphenylethyl, 1-phenylpropyl, 2-phenylpropyl, 3-phenylpropyl, 4-phenylbutyl, 5-phenylpentyl or the like, among which $C_{7-13}$ aralkyl (e.g. benzyl) is preferable.

Among the hydrocarbon groups as mentioned above, $C_{1-6}$ alkyl is preferable, and n-butyl or tert-butyl is particularly preferable.

The substituents of these hydrocarbon groups include, but are not limited to, for example, (i) halogen (e.g. fluorine, chlorine, bromine or iodine), (ii) $C_{1-3}$ alkylenedioxy (e.g. methylenedioxy or ethylenedioxy), (iii) nitro, (iv) cyano, (v) optionally halogenated $C_{1-6}$ alkyl (e.g. methyl, ethyl, n-propyl or trifluromethyl), (vi) optionally halogenated $C_{1-6}$ alkenyl (e.g. vinyl, allyl or isopropenyl), (vii) optionally halogenated $C_{1-6}$ alkynyl (e.g. propargyl, ethynyl, butynyl or 1-hexynyl), (viii) $C_{3-6}$ cycloalkyl optionally substituted by halogen, $C_{1-3}$ alkylenedioxy, nitro, cyano or optionally halogenated $C_{1-6}$ alkyl, (ix) optionally halogenated $C_{1-6}$ alkoxy, (x) optionally halogenated $C_{1-6}$ alkylthio, (xi) amino protected by known monovalent or divalent amino-protecting groups such as phthaloyl,

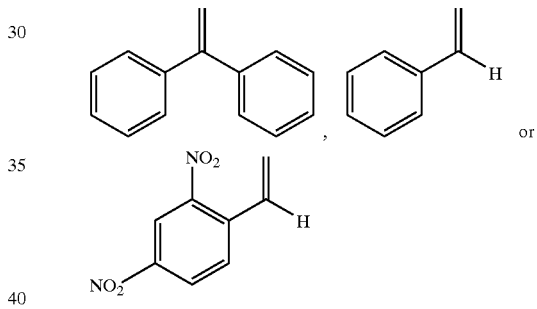

said monovalent amino-protecting groups being, for example, benzyl, p-methoxybenzyl, p-nitrobenzyl, benzhydryl, formyl, acetyl, propionyl, phenylacetyl, phenoxyacetyl, pivaloyl, methoxycarbonyl, ethoxycarbonyl, isobutoxycarbonyl, t-butoxycarbonyl, 2-propenyloxycarbonyl, benzyloxycarbonyl or p-nitrobenzyloxycarbonyl), (xii) di-$C_{1-6}$ alkylamino (e.g. dimethylamino, dipropylamino or dibutylamino), (xiii)5- or 6-membered cyclic amino (e.g. morpholino, thiomorpholino, piperidino or pyrrolidin-1-yl), (xiv) $C_{1-6}$ alkyl-carbonyl (e.g. acetyl or propionyl), (xv) $C_{1-6}$ alkoxy-carbonyl (e.g. methoxycarbonyl, ethoxycarbonyl, propoxycarbonyl or butoxycarbonyl), (xvi) $C_{1-6}$ alkylsulfonyl (e.g. methylsulfonyl or ethylsulfonyl), (xvii) $C_{6-10}$ aryl (e.g. phenyl or naphthyl) optionally substituted by halogen, $C_{1-3}$ alkylenedioxy, nitro, cyano or optionally halogenated $C_{1-6}$ alkyl, (xviii) $C_{7-15}$ aralkyl (e.g. benzyl, phenethyl, 2-phenylethyl, 1-phenylpropyl, 2-phenylpropyl or naphthylmethyl) optionally substituted by halogen, $C_{1-3}$ alkylenedioxy, nitro, cyano or optionally halogenated $C_{1-6}$ alkyl, (xix) $C_{6-10}$ aryloxy (e.g. phenoxy or naphthyloxy) optionally substituted by halogen, $C_{1-3}$ alkylenedioxy, nitro, cyano or optionally halogenated $C_{1-6}$ alkyl, (xx) $C_{7-16}$ aralkyloxy (e.g. benzyloxy) optionally substituted by halogen, $C_{1-3}$ alkylenedioxy, nitro, cyano or optionally halogenated $C_{1-6}$ alkyl, (xxi) oxo, (xxii) di-$C_{1-6}$ alkylthiocarbamoyl (e.g. dimethylthiocarbamoyl or diethylthiocarbamoyl), (xxiii) $C_{6-10}$ aryl-carbonyloxy (e.g. phenylcarbonyloxy), (xxiv) $C_{6-14}$ arylsulfonamide (e.g. phenylsulfonamide), and (xxv) $C_{1-6}$ alkylsulfonamide (e.g. methylsulfonamide or ethylsulfonamide).

The magnesium compound (I) can be preferably a compound represented by the formula:

$$R^{1'}\text{—Mg—}X^1 \qquad (I')$$

(wherein $R^{1'}$ is a halogen atom, $C_{1-12}$ alkyl, $C_{2-4}$ alkenyl, $C_{6-10}$ aryl or $C_{7-13}$ aralkyl, and $X^1$ is a halogen atom)

Examples of $C_{1-12}$ alkyl, $C_{2-4}$ alkenyl, $C_{6-10}$ aryl or $C_{7-13}$ aralkyl represented by $R^{1'}$ are the same as those defined above for the hydrocarbon groups represented by $R^1$.

Examples of the halogen atoms represented by $R^{1'}$ and $X^1$ are the same as those defined above for $R^1$ and X.

Typically the magnesium compounds (I) include, for example, magnesium bromide, magnesium iodide, magnesium chloride, magnesium fluoride, dimethylmagnesium iodide, methylmagnesium chloride, methylmagnesium iodide, methylmagnesium chloride, methylmagnesium iodide, diethylmagnesium, ethylmagnesium chloride, ethylmagnesium bromide, ethylmagnesium iodide, dipropylmagnesium, propylmagnesium chloride, propylmagnesium bromide, propylmagnesium iodide, diisopropylmagnesium, isopropylmagnesium chloride, isopropylmagnesium bromide, isopropylmagnesium iodide, di-n-butylmagnesium, n-butylmagnesium chloride, n-butylmagnesium bromide, n-butylmagnesium iodide, di-sec-butylmagnesium, sec-butylmagnesium chloride, sec-butylmagnesium bromide, sec-butylmagnesium iodide, di-tert-butylmagnesium, tert-butylmagnesium chloride, tert-butylmagnesium bromide, tert-butylmagnesium iodide, diphenylmagnesium, phenylmagnesium chloride, phenylmagnesium bromide, phenylmagnesium iodide, divinylmagnesium, vinylmagnesium chloride, vinylmagnesium bromide, vinylmagnesium iodide, diallylmagnesium, allylmagnesium chloride, allylmagnesium bromide, allylmagnesium iodide, di(2-furyl)magnesium, 2-furylmagnesium chloride, 2-furylmagnesium bromide, 2-furylmagnesium iodide, di(3-furyl)magnesium, 3-furylmagnesium chloride, 3-furylmagnesium bromide, 3-furylmagnesium iodide, di(2-thienyl)magnesium, 2-thienylmagnesium chloride, 2-thienylmagnesium bromide, 2-thienylmagnesium iodide, di(3-thienyl)magnesium, 3-thienylmagnesium chloride, 3-thienylmagnesium bromide, 3-thienylmagnesium iodide, dibenzylmagnesium, benzylmagnesium chloride, benzylmagnesium bromide or benzylmagnesium iodide, among which n-butyl magnesium or n-butylmagnesium is especially preferable.

The organolithium compound (II) can be preferably a compound represented by the formula:

$$R^{2'}\text{—Li} \qquad (II')$$

(wherein $R^{2'}$ is $C_{1-12}$ alkyl, $C_{2-4}$ alkenyl, $C_{6-10}$ aryl or $C_{7-13}$ aralkyl).

The $C_{1-12}$ alkyl, $C_{2-4}$ alkenyl, $C_{6-10}$ aryl and $C_{7-13}$ aralkyl groups represented by $R^{2'}$ are the same as those except for the halogen atom in the definition of $R^{1'}$ described above.

Typically, the organolithium compounds (II) include, for example, ethyllithium, propyllithium, n-butyllithium, sec-butyllithium, isobutyllithium, tert-butyllithium, methyllithium, 2-furyllithium, vinyllithium, allyllithium, benzyllithium, 2-thienyllithium or phenyllithium, among which n-butyllithium is particularly preferred.

The mixture of magnesium compound (I) and organolithium compound (II) can be prepared by mixing the two compounds together in an arbitrary proportion. It is preferred to add about one to four moles of the organolithium compound (II) per mole of the magnesium compound (I). Examples of the reaction products from the magnesium compound (I) and the organilithium compound (II) are a compound represented by the formula:

$$(R^a R^b R^c Mg)^{2-}\cdot Li^+ \qquad (III)$$

(wherein $R^a$, $R^b$, and $R^c$ are the same or different and are each a hydrocarbon residue which may be substituted) and a compound represented by the formula:

$$(R^d R^e R^f R^g Mg)^{2-}\cdot 2Li^+ \qquad (IV)$$

(wherein $R^d$, $R^e$, $R^f$, and $R^g$ are the same or different and are each a hydrocarbon residue which may be substituted).

In the above formulae, examples of the optionally substituted hydrocarbon residues represented by $R^a$, $R^b$, $R^c$, $R^d$, $R^e$, $R^f$, and $R^g$ are the same as those defined above for $R^1$ and $R^2$, among which $C_{1-6}$ alkyl, particularly n-butyl, is preferred.

Typically tri-n-butylmagnesium lithium or the like is preferably used as the compound (III).

As the compound (IV) is preferably used tetra-n-butylmagnesium dilithium or the like.

The magnesium compounds (I), the organolithium compounds (II), and a mixture of (I) and (II) can be prepared according to per se known methods.

The mixture of the magnesium compounds (I) and the organolithium compounds (II) are novel.

The reaction product from the magnesium compound (I) and the organolithium compound (II) can be, for example, prepared by allowing both compounds to react in an inert solvent.

The inert solvent used in the present reaction can be any solvents used in halogen-metal exchange reaction with Grignard reagents and organolithium compounds. Typically, toluene, xylene, tetrahydrofuran, diethyl ether, dimethoxyethane or a mixture thereof is preferably used.

The magnesium compound (I) is usually used in approximately 0.25 to 1.0 molar equivalent to the organolithium compound (II).

The reaction temperature is usually about −10° C. to room temperature, preferably about −10° C. to 0° C.

The reaction time is usually about 5 minutes to 2 hours, preferably about 15 minutes to one hour.

The mixture of the compound (I) and the organolithium compound (II) or their reaction product, thus obtained in the present invention, is isolated and purified, or may be served without isolation as an exchange reagent for the functional groups in the halogen-metal exchange reaction as hereinafter described.

By use of the present exchange reagents, the halogen-metal exchange reaction can be effected under milder conditions, i.e., at about −10° C. to room temperature (about 10° C. to 40° C.), different from extreme low temperature.

The substitution process of the present invention relates to a process for substituting a halogen atom present in halogenated compounds with an electrophilic group, which comprises reacting (i) a halogenated compound having in the molecule at least one halogen atom or one double or triple bond to which is attached a halogen-substituted carbon atom, with (ii) an exchange reagent as hereinbefore described, reacting the resultant product with (iii) a compound having an electrophilic group, and optionally hydrolyzing the resultant product.

The term "a halogenated compound having in the molecule at least one halogen atom or one double or triple bond" means starting materials employed in the halogen-metal exchange reaction, such as Grignard reagents and/or organolithium compounds.

These halogenated compounds are exemplified by (1) a compound of the formula:

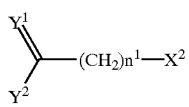

(V)

(wherein $Y^1$ is a divalent organic residue, $Y^2$ is a monovalent organic residue, or $Y^1$ and $Y^2$, taken together, may form a trivalent organic residue, $X^2$ is a halogen atom, and $n^1$ is 0 or 1), (2) a compound of the formula:

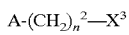

(VI)

(wherein A is an optionally substituted aromatic ring, $n^2$ is 0 or 1, and $X^3$ is a halogen atom), (3) a compound of the formulae:

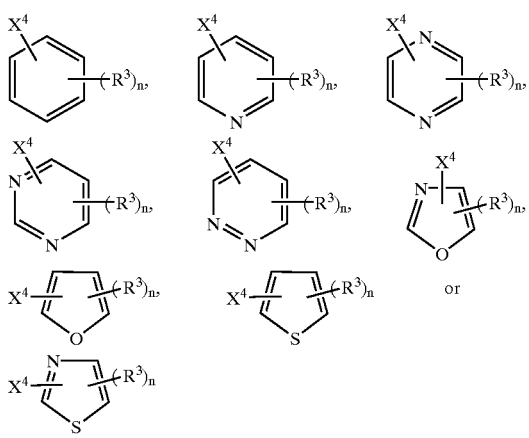

(VII)

(wherein $X^4$ is a halogen atom, $R^3$ is a hydrogen atom, a protected amino group, an optionally substituted hydrocarbon group, an optionally substituted hydrocarbon-oxy group or a halogen atom and n is 1 or 2), and (4) a compound of the formula:

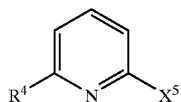

(VIII)

(wherein $R^4$ is a hydrogen atom, a protected amino group, an optionally substituted hydrocarbon group, an optionally substituted hydrocarbon-oxy group or a halogen atom, and $X^5$ is a halogen atom).

The halogen atoms represented by $X^2$, $X^3$, $X^4$, $X^5$, $R^3$ and $R^4$ are the same as those defined above for $X^1$, among which bromine is preferable.

The optionally substituted hydrocarbon groups represented by $R^3$ and $R^4$ are the same as those defined above for $R^1$ which is an optionally substituted hydrocarbon group.

The optionally substituted hydrocarbon-oxy groups can be a group represented by the formula: —$OR^5$ ($R^5$ is an optionally substituted hydrocarbon group). The optionally substituted hydrocarbon groups represented by $R^5$ are the same as those defined above for $R^1$.

The protected amino groups represented by $R^3$ and $R^4$ are the same as those described above for (xii) as a substituent of $R^1$ which is an optionally substituted hydrocarbon group.

The divalent organic groups represented by $Y^1$ can be an organic residue which is capable of attaching to the adjacent carbon atom via a double bond, and include, for example, (1) a group represented by the formula:

(wherein $Y^3$ is a hydrogen atom, an optionally substituted hydrocarbon group or an optionally substituted heterocyclic group, $R^f$ is a hydrogen atom or a $C_{1-6}$ alkyl group (e.g. methyl, ethyl, propyl or n-butyl) and (2) a group represented by the formula:

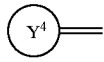

(wherein $Y^4$ is an optionally substituted 3- to 8-membered carbocyclic group).

The optionally substituted hydrocarbon groups represented by $Y^3$ are the same as those described above for $R^1$ which is an optionally substituted hydrocarbon group, among which optionally halogenated $C_{1-6}$ alkyl (e.g. methyl, ethyl) or optionally halogenated $C_{2-6}$ alkenyl (e.g. ethenyl, propenyl) are preferred, and particularly $C_{1-6}$ alkyl is preferable.

The optionally substituted heterocycles represented by $Y^3$ can be, for example, 5- to 8-membered monocyclic non-aromatic heterocycles, monocyclic aromatic heterocycles, or benzene-fused or naphthalene-fused aromatic heterocycles, containing one or more hetero atoms (e.g. one to four hetero atoms, preferably one to three hetero atoms) selected from nitrogen, sulfur and oxygen other than carbon. Typically such heterocycles include, for example, pyrrolidine, piperidine, piperazine, morpholine, thiophene, benzo(b) thiophene, benzo(b)furan, benzimidazole, benzoxazole, benzothiazole, benzisothiazole, naphth(2,3-b)thiophene, thianthrene, furan, isoindolizine, xanthlene, phenoxathiin, pyrrole, imidazole, triazole, thiazole, oxazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, isothiazole, phenothiazine, isoxazole, furazane, phenoxazine, isochromane, or so forth, among which a monovalent group formed by removing one hydrogen atom in the ring of pyridine, thiophene or furan is preferred, and pyridyl, furyl, or thiazolyl are particularly preferable.

Among the optionally substituted heterocyclic groups represented by $Y^3$ as exemplified above, the NH group, if present, in the heterocyclic ring of pyrrolidine, piperidine, piperazine, morpholine, benzimidazole, isoindolizine, imidazole, triazole, pyrazole, indole, isoindole, 1H-indazole, purine, carbazole, β-carboline, phenothiazine or phenoxazine is protected by known amino-protecting groups (e.g. benzyl).

The substituents of these heterocycles are the same as those of the optionally substituted hydrocarbon groups represented by $R^1$ as described above.

$R^f$ is preferably a hydrogen atom.

The 3- to 8-membered carbocyclic groups represented by $Y^4$ are exemplified by 3- to 8-membered saturated carbocycles or 3- to 8-membered unsaturated carbocycles, and include, for example, 3- to 8-membered cycloalkanes (e.g. cyclopropane, cyclobutane, cyclopentane, cyclohexane, cycloheptane, cyclooctane), cycloalkenes (e.g. cyclobutene, cyclopentene, cyclohexene, cycloheptene, cyclooctene), cycloalkane-dienes (e.g. cycloheptane-diene, cyclohexane-diene, cycloheptane-diene, cyclooctane-diene), among which 5- to 7-membered cycloalkanes (e.g. cyclopentane, cyclohexane, cycloheptane) are preferred.

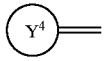

Typically a group represented by the formula: includes preferably, for example,

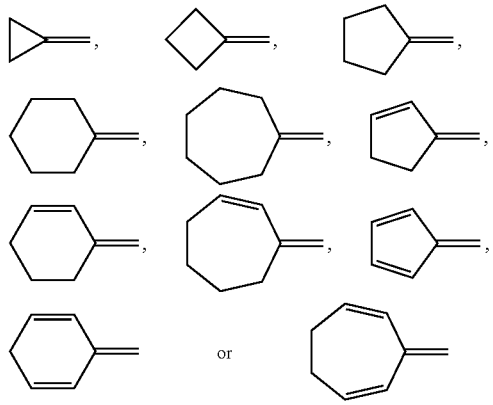

Examples of the substituents on the 3- to 7-membered carbocycles are halogen (e.g. fluorine, chlorine or bromine), hydroxyl, carboxy, or $C_{1-6}$ alkoxy-carbonyl (e.g. acetoxy or ethoxycarbonyl).

The monovalent organic residue represented by $Y^2$ is a group formed by removing one arbitrary hydrogen atom from an organic group. Examples of such groups are an optionally substituted hydrocarbon group, an optionally substituted heterocyclic group, a group represented by the formula: —$NY^5Y^6$ (wherein $Y^5$ and $Y^6$ are independently an optionally substituted hydrocarbon group, an optionally substituted heterocyclic group and an acyl group), a group represented by the formula: —O—$Y^7$ (wherein $Y^7$ is a hydrogen atom, an optionally substituted hydrocarbon group or an optionally substituted heterocyclic group) or a group represented by the formula: —S—$Y^8$ (wherein $Y^8$ is a hydrogen atom, an optionally substituted hydrocarbon group or an optionally substituted heterocyclic group).

The optionally substituted hydrocarbon groups represented by $Y^2$, $Y^5$, $Y^6$, $Y^7$ and $Y^8$ are the same as those defined above for $R^1$ which is an optionally substituted hydrocarbon group, among which $C_{1-6}$alkyl groups (e.g. methyl or ethyl) which may be halogenated are preferred.

The optionally substituted heterocyclic groups represented by $Y^2$, $Y^5$, $Y^6$, $Y^7$ and $Y^8$ are the same as those defined above for $Y^3$ which is an optionally substituted heterocyclic group.

The acyl groups represented by $Y^5$ and $Y^6$ can be a group represented by the formula: —CO—$Y^9$ wherein $Y^9$ is an optionally substituted hydrocarbon group. The optionally substituted hydrocarbon groups represented by $Y^9$ are the same as those defined above for $R^1$ which is an optionally substituted hydrocarbon group, among which $C_{1-6}$ alkyl groups (e.g. methyl, ethyl) which may be halogenated are preferred.

The trivalent organic residues formed when $Y^1$ and $Y^2$ are taken together, and represented by the formula:

are, for example,

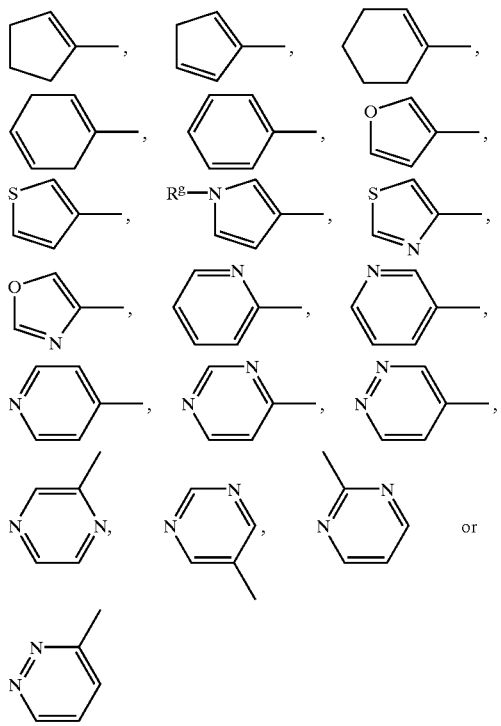

$R^9$ is a known amino-protecting group such as benzyl or the like.

Examples of the aromatic rings in the optionally substituted aromatic rings are aromatic hydrocarbon groups or aromatic heterocyclic groups.

The aromatic hydrocarbon groups include monocyclic, fused polycyclic, or polycondensed aromatic hydrocarbons, having 6 to 14 carbon atoms. Typical examples of such aromatic hydrocarbons are $C_{6-14}$ aryl, including phenyl, biphenylyl, naphthyl (e.g. 1-naphthyl or 2-naphthyl), indenyl (e.g. 2-indenyl), anthlyl (e.g. 1-anthlyl, 2-anthlyl or 3-anthlyl) or phenanthlyl (e.g. 1-phenanthlyl, 2-phenanthlyl, 3-phenanthlyl, 4-phenanthlyl or 9-phenanthlyl), among which phenyl, biphenylyl, 1-naphthyl, 2-naphthyl or the like are preferable, and phenyl is particularly preferable.

The aromatic heterocyclic groups can be, for example, 5- to 8-membered monocyclic aromatic heterocycles, or benzene-fused or naphthalene-fused aromatic heterocycles, containing one or more hetero atoms (e.g. one to four hetero atoms, preferably one to three hetero atoms) selected from nitrogen, sulfur and oxygen other than carbon. Typically such heterocycles include, for example, thiophene, benzo (b)thiophene, benzo(b)furan, benzimidazole, benzoxazole, benzothiazole, benzisothiazole, benzisothiazole, naphth(2,3-b)thiophene, thianthrene, furan, isoindolizine, xanthlene, phenoxathiin, pyrrole, imidazole, triazole, thiazole, oxazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, isothiazole, phenothiazine, isoxazole, furazane, phenoxazine, isochromane, or a monovalent group formed by removing one hydrogen atom from the rings fused with one or more (preferably one to two, especially one) benzene or naphthyl rings, among which pyridyl, pyrimidinyl, pyrazinyl or furyl is preferred.

Among the aromatic heterocycles as exemplified above, the NH group, if any, on the heterocyclic ring such as benzimidazole, isoindolizine, pyrrole, imidazole, triazole, pyrazole, indole, isoindole, 1H-indazole, purine, carbazole, β-carboline, phenothiazine or phenoxazine is protected by known amino-protecting groups (e.g. benzyl).

The substituents of these aromatic groups are the same as those of the hydrocarbon groups described above for $R^1$.

Among others as described above, the symbol "A" can be preferably 5- to 8-membered monocyclic aromatic heterocycles containing one to three hetero atoms selected from nitrogen, sulfur and oxygen other than carbon. In particular, pyridyl, pyrimidinyl, pyrazinyl or furyl is preferred.

As the compound (V) is preferred a compound when $Y^1$ is (i) a group of the formula: $Y^{3'}$—CH=(wherein $Y^{3'}$ is $C_{1-6}$ alkyl) or (ii) a group of the formula:

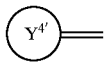

(wherein $Y^{4'}$ is a 3- to 8-membered cycloalkane), $Y^2$ is $C_{1-6}$ alkyl, $n^1$ is 0 or 1, and $X^2$ is chlorine or bromine.

As the compound (VI) is preferred a compound when A is phenyl, pyrazyl or furyl, all these being optionally substituted by halogen, halogenated $C_{1-6}$ alkyl or optionally halogenated $C_{1-6}$ alkoxy, $n^2$ is 0 or 1, and $X^3$ is chlorine or bromine.

As the compound (VII) is preferred a compound when $R^3$ is amino protected by, for example, pivaloyl, benzyl, phthaloyl or t-butoxycarbonyl, halogen (e.g. chlorine or bromine), $C_{1-6}$ alkyl or $C_{1-6}$ alkoxy, and $X^4$ is chlorine or bromine.

As the compound (VIII) is preferred a compound when $R^4$ is amino protected by, for example, pivaloyl, benzyl, phthaloyl or t-butoxycarbonyl, halogen (e.g. chlorine or bromine), $C_{1-6}$ alkyl or $C_{1-6}$ alkoxy, and $X^4$ is chlorine or bromine.

Among the halogenated compounds as described above is preferred a compound represented by the formula (VIII). Particularly, 2,6-dibromopyridine or a compound represented by the formula:

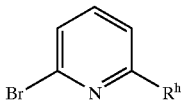

(wherein $R^h$ is an amino group protected by pivaloyl, benzyl, phthaloyl or t-butoxycarbonyl) are preferred.

The aforementioned reagents for exchange reaction of the present invention can be employed as an exchange reagent.

In particular, the magnesium compounds include preferably n-butylmagnesium bromide and n-butylmagnesium chloride, and the organolithium compounds include preferably n-butyl-lithium.

As the compound (III) is preferred tri-n-butylmagnesium lithium, and as the compound (IV) is preferable, for example, tetra-n-butylmagnesium dilithium.

The compounds having an electrophilic group can be any kind of molecules capable of accepting an electron, preferably compounds with high electron density capable of reacting with lone electron pair. Since the exchange reaction of the present invention is an improved halogen-metal exchange reaction with Grignard reagents and/or organolithium reagents, the aforementioned electrophilic compounds mean any electrophilic reagents employed for the halogen-metal exchange reaction, such as Grignard reagents and/or organolithium compounds.

Typically the compounds having an electrophilic group include, for example, halogen (e.g. chlorine, bromine or iodine), carbon dioxide, solid sulfur, sulfur dioxide, oxygen or compounds represented by the formulae (1) to (21) given below.

The definitions of symbols in the formulae (1) to (21) are as follows:

The term "$C_{5-12}$ aryl" means, for example, cyclopentadienyl, phenyl, indenyl, biphenylyl or naphthyl, among which phenyl is preferred.

The term "$C_{1-12}$ alkyl" means, for example, a linear or branched alkyl group such as methyl, ethyl, propyl, isopropyl, butyl, isobutyl, t-butyl, pentyl, hexyl, heptyl, octyl, nonyl, decyl, undecyl, dodecyl or the like, among which methyl, ethyl, propyl, isopropyl, butyl, butyl, pentyl, decyl, dodecyl or the like are preferable, and methyl, ethyl, propyl, butyl, hexyl or dodecyl is particularly preferred.

The term "$C_{1-4}$ alkyl" means, for example, a linear or branched alkyl group such as methyl, ethyl, propyl, isopropyl, butyl, isobutyl or t-butyl, among which methyl, ethyl, propyl, isopropyl or butyl is preferable, and methyl, ethyl, propyl, or butyl is particularly preferable.

The term "$C_{2-4}$ alkenyl" means, for example, a linear alkenyl group such as vinyl, allyl, 1-butenyl or 2-butenyl, among which vinyl or allyl is preferable.

The term "$C_{6-10}$ aryl" means, for example, an aryl group such as phenyl, o-tolyl, m-tolyl, p-tolyl, o-anisyl, m-anisyl, p-anisyl, 1-naphthyl or 2-naphthyl, among which phenyl, p-tolyl, p-anisyl or 2-naphthyl is preferable.

The term "$C_{6-10}$ arylthio" means, for example, an arylthio group such as phenylthio, o-tolylthio, m-tolylthio, p-tolylthio, o-anisylthio, m-anisylthio, p-anisylthio, 1-naphthylthio or 2-naphthylthio, among which phenylthio, p-tolylthio, p-anisylthio or 2-naphthylthio is preferable.

The term "$C_{7-13}$ aralkyl" means, for example, an aralkyl group such as benzyl, o-tolylmethyl, m-tolylmethyl, p-tolylmethyl, o-anisylmethyl, m-anisylmethyl, p-anisylmethyl, benzhydryl, 1-naphthylmethyl or 2-naphthylmethyl, among which benzyl, p-tolylmethyl, p-anisylmethyl or 2-naphthylmethyl is preferable.

The term "$C_{4-8}$ heteroaryl" means, for example, a heteroaryl group such as 2-thienyl, 3-thienyl, 2-furyl, 3-furyl, benzofuranyl or benzothienyl, among which 2-thienyl, 3-thienyl, 2-furyl or 3-furyl is preferable.

The term "$C_{1-4}$ alkoxy" means, for example, a linear or branched alkoxy group such as methoxy, ethoxy, propoxy, isopropoxy, butoxy, isobutoxy or tert-butoxy, among which methoxy, ethoxy, propoxy or butoxy is preferable, and in particular methoxy, ethoxy or butoxy is preferred.

The term "$C_{2-5}$ alkoxycarbonylamino" means, for example, a linear or branched alkoxy group such as methoxycarbonylamino, ethoxycarbonylamino, propoxycarbonylamino, isopropoxycarbonylamino, butoxycarbonylamino, isobutoxycarbonylamino or t-butoxycarbonylamino, among which methoxycarbonylamino, ethoxycarbonylamino, propoxycarbonylamino, or butoxycarbonylamino is preferable, and methoxycarbonylamino, ethoxycarbonylamino, or butoxycarbonylamino is particularly preferred.

The term "$C_{1-4}$ alkylthio" means, for example, a linear or branched alkylthio group such as methylthio, ethylthio, propylthio, isobutylthio, butylthio, isobutylthio or t-butylthio, among which methylthio, ethylthio, propylthio, and butylthio are preferable, and methylthio, ethylthio or butylthio is particularly preferred.

The term "$C_{1-4}$ alkylamino" means, for example, a linear or branched alkylamino group such as methylamino, ethylamino, propylamino, isopropylaminoi, butylamino, isobutylamino or t-butylamino, among which methylamino, ethylamino, propylamino, butylamino, isobutylamino or t-butylamino is preferable, and methylamino, ethylamino or butylamino is particularly preferred.

The term "N,N-di-$C_{1-4}$ alkylamino" means, for example, a di-linear or branched alkylamino group such as dimethylamino, diethylamino, dipropylamino, diisopropylamino, dibutylamino, diisobutylamino or di-t-butylamino, among which dimethylamino, diethylamino, dipropylamino, dibutylamino, diisobutylamino or di-t-butylamino is preferable, and dimethylamino, diethylamino, or dibutylamino is particularly preferable.

The term "$C_{5-12}$ aryl" means, for example, cyclopentadienyl, phenyl, indenyl, biphenylyl and naphthyl, among which phenyl is preferable.

The term "$C_{4-10}$ heterocyclic group" means a heterocyle which contains, as a hetero atom, one to four groups selected from oxygen, a group of the formula: $S(\rightarrow O)_n^3$ ($n^3$ is 0, 1 or 2), a group of the formula: $N \rightarrow O$, a group of the formula: $=N-$ and a group of the formula: $NR^5$ ($R^5$ is $C_{1-4}$ alkyl or benzyl), such as furyl, thienyl, 1-benzylpyrrol, 1-benzylimidazolyl, quinolyl, isoquinolyl, pyridyl, indolyl, pyrimidinyl or piperazinyl, among which furyl, thienyl, 1-benzylpyrrol, 1-benzylimidazolyl, quinolyl, isoquinolyl, or pyridyl is preferred.

The term "$C_{7-13}$ aralkyl" means, for example, an aralkyl group such as benzyl, phenethyl, indenylmethyl, biphenylylmethyl or naphthylmethyl, among which benzyl and naphthylmethyl is preferable.

The term "$C_{1-4}$ alkylsulfonyl" means, for example, a linear or branched alkylsulfonyl group such as methylsulfonyl, ethylsulfonyl, propylsulfonyl, isopropylsulfonyl, butylsulfonyl, isobutylsulfonyl and t-butylsulfonyl, among which methylsulfonyl, ethylsulfonyl, propylsulfonyl, butylsulfonyl or t-butylsulfonyl is preferable, and methylsulfonyl, ethylsulfonyl or butylsulfonyl is particularly preferred.

The term "$C_{1-5}$ alkanoyl" means, for example, a linear or branched alkanoyl such as acetyl, propionyl, butyryl, isobutyryl, valeryl or pivaloyl, among which acetyl, butyryl, isobutyryl or pivaloyl is preferable, and acetyl, butyryl, or pivaloyl is particularly preferred.

The term "$C_{1-5}$ alkoxycarbonyl" means, for example, a linear or branched alkoxycarbonyl group such as methoxycarbonyl, ethoxycarbonyl, propoxycarbonyl, isopropoxycarbonyl, butoxycarbonyl, isobutoxycarbonyl or t-butoxycarbonyl, among which ethoxycarbonyl, propoxycarbonyl, butoxycarbonyl or t-butoxycarbonyl is preferable, and ethoxycarbonyl, butoxycarbonyl or t-butoxycarbonyl is particularly preferred.

The term "$C_{3-12}$ alkylene" means, for example, a linear alkylene group such as trimethylene, tetramethylene, pentamethylene, hexamethylene, heptamethylene, octamethylene, nonamethylene, decamethylene, undecamethylene or dodecamethylene, among which trimethylene, tetramethylene, pentamethylene, nonamethylene, decamethylene, undecamethylene or dodecamethylene is preferable, and trimethylene, tetramethylene, decamethylene, undecamethylene or dodecamethylene is particularly preferred.

The term "$C_{4-7}$ alkylene" means, for example, a linear alkylene group such as tetramethylene, pentamethylene, hexamethylene or heptamethylene, among which tetramethylene, pentamethylene or hexamethylene is preferable, and tetramethylene or pentamethylene is particularly preferred.

(1) A compound represented by the formula:

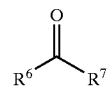

(1)

(wherein $R^6$ and $R^7$ are independently hydrogen, $C_{1-4}$ alkyl, halogen, $C_{1-4}$ lower alkoxy, $C_{1-4}$ alkylthio, $C_{6-10}$ arylthio, N,N-di-$C_{1-4}$ alkylamino, $C_{5-12}$ aryl, or $C_{4-10}$ heterocycle (optionally containing one to four hetero atoms selected from oxygen, a group of the formula: $S(\rightarrow O)_n^4$ ($n^4$ is 0, 1 or 2), a group of the formula: $N \rightarrow O$, a group of the formula: $=N-$, or a group of the formula: $NR^8$ ($R^8$ is $C_{1-4}$ alkyl or benzyl)).

Typical examples of compounds (1) used are N,N-dimethylformamide, ethyl formate, N,N-dimethylaminocarbonyl chloride, N,N-dimethylacetamide, acetyl chloride, ethyl benzoate, diethyl carbonate, ethyl chlorocarbonate, benzophenone, benzaldehyde, ethyl chlorothiocarbonate, and the like.

(2) An acid anhydride represented by the formula:

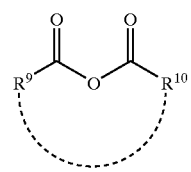

(2)

(wherein $R^9$ and $R^{10}$ are independently $C_{1-4}$ alkyl, $C_{5-12}$ aryl, $C_{7-13}$ aralkyl, or $C_{4-10}$ heterocycle (optionally containing one to four hetero atoms selected from oxygen, a group of the formula: $S(\rightarrow O)_n^5$ ($n^5$ is 0, 1 or 2), a group of the formula: $N \rightarrow O$, a group of the formula: $=N-$, and a group of the formula: $NR^{11}$ ($R^{11}$ is $C_{1-4}$ alkyl or benzyl), or $R^9$ and $R^{10}$, taken together, may form $C_{2-4}$ alkylene or phenylene)

Typical examples of compound (2) used are acetic anhydride, succinic anhydride, propionic anhydride, benzoic anhydride and maleic anhydride.

(3) A compound represented by the formula:

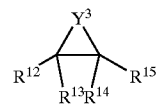

(3)

(wherein $R^{12}$, $R^{13}$, $R^{14}$ and $R^{15}$ are independently hydrogen, $C_{1-4}$ alkyl or phenyl, or either of $R^{12}$ and $R^{13}$ and either of $R^{14}$ and $R^{15}$, taken together, may form $C_{3-12}$ alkylene, and $Y^3$ is oxygen or a group of the general formula: $N-R^{16}$ ($R^{16}$ is $C_{1-4}$ alkyl, $C_{1-4}$ alkylsulfonyl, $C_{1-5}$ alkanoyl, $C_{1-5}$ alkoxycarbonyl or a group of the general formula: $S(\rightarrow O)_n^6$ ($n^6$ is 0, 1 or 2)).

Typical examples of compound (3) used are aziridines, and ethylene oxide derivatives such as ethylene oxide, 2-methyl-1,2-epoxypropane, 7-thiabicyclo(4,1,0)heptane, 6-thiabicyclo(3,1,0)hexane, 7-oxabicyclo(4,1,0)heptane, 6-oxabicyclo(3,1,0)hexane, 7-azabicyclo(4,1,0)heptane, 6-azabicyclo(3,1,0)hexane, 7-ethoxycarbonyl-7-azabicyclo(4,1,0)heptane and 6-ethoxycarbonyl-6-azabicyclo(3,1,0)hexane.

(4) An α,β-unsaturated carbonyl compound represented by the formula:

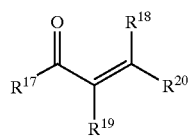

(4)

(wherein $R^{17}$, $R^{18}$, $R^{19}$ and $R^{20}$ are independently hydrogen, $C_{1-4}$ alkyl or phenyl).

Typical examples of compound (4) used are α,β-unsaturated ketone derivatives such as 3-oxo-1,3-diphenyl-1-propene and 2-methyl-3-oxo-3-diphenyl-1-propene.

(5) A halogenated ethane represented by the formula:

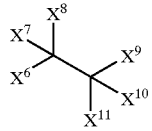

(5)

(wherein $X^6$, $X^7$, $X^8$, $X^9$, $X^{10}$ and $X^{11}$ are independently hydrogen or halogen, provided that at least one of $X^6$, $X^7$ and $X^8$ is halogen, and at lest one of $X^9$, $X^{10}$ and $X^{11}$ is halogen).

Typical examples of compound (5) used are halogenated ethanes such as hexachloroethane, hexafluoroethane, 1,1,2,2-tetrabromoethane, 1,2-dibromoethane, 1,2-dilodoethane, pentafluoroiodoethane, 1,2-dibromo-1,1,2,2-tetrafluoroethane, 1,2-dichloro-1,1,2,2-tetrafluroethane, 1,1,1-trichloro-2,2,2-trifluoroethane and 2,2-trifluoroethane-2,2,1-trichloroethane.

(6) A compound represented by the formula:

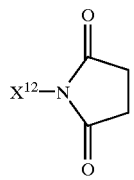

(6)

(wherein $X^{12}$ is halogen).

Typical examples of compounds (6) used are succinimides such as N-iodosuccinimide, N-bromosuccinimide and N-chlorosuccinimide.

(7) A compound represented by the formula:

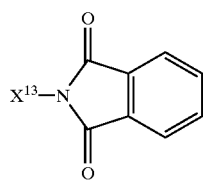

(7)

(wherein $X^{13}$ is halogen).

Typical examples of compounds (7) used are phthalimides such as N-bromophthalimide and N-chlorophthalimide.

(8) A compound represented by the formula:

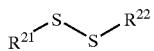

(8)

(wherein $R^{21}$ and $R^{22}$ are independently $C_{1-4}$ alkyl or phenyl).

Typical examples of compounds (8) used are disulfide derivatives such as dimethyl disulfide, diethyl disulfide, dipropyl disulfide, dibutyl disulfide and diphenyl disulfide.

(9) A compound represented by the formula:

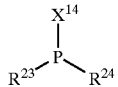

(9)

(wherein $X^{14}$ is halogen, and $R^{23}$ and $R^{24}$ are independently $C_{1-4}$ alkyl or phenyl).

Typical examples of compounds (9) used are phosphine derivatives such as chlorodiphenylphosphine, chlorodimethylphosphine, bromodiphenylphosphine and bromodimethylphosphine.

(10) A compound represented by the formula:

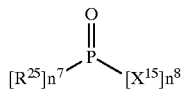

(10)

(wherein $X^{15}$ is halogen or phenyl, $R^{25}$ is $C_{1-4}$ alkyl, phenyl, $C_{1-4}$ alkoxy, di-$C_{1-4}$ alkylamino or $C_{2-5}$ alkoxycarbonylamino, $n^7$ is 0, 1 or 2, and $n^8$ is 1, 2 or 3).

Typical examples of compounds (10) used are dimethyl chlorophosphonate, triphenylphosphine oxide and diphenyl chlorophosphonate.

(11) A compound represented by the formula:

(11)

(wherein $R^{26}$ is $C_{1-4}$ alkyl or phenyl).

Typical examples of compounds (11) used are acetonitrile, propionitrile, butyronitrile and benzonitrile.

(12) A compound represented by the formula:

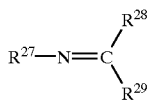

(12)

(wherein $R^{27}$ is $C_{1-4}$ alkyl, di-$C_{1-4}$ alkylamino, hydroxyl, or $C_{1-4}$ alkoxy, and $R^{28}$ and $R^{29}$ are independently $C_{1-4}$ alkyl or phenyl).

Typical examples of compounds (12) used are benzophenoneimine and acetone-oxime.

(13) A compound represented by the formula:

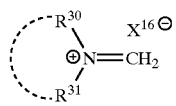

(13)

(wherein $R^{30}$ and $R^{31}$ are independently $C_{1-4}$ alkyl or phenyl, or $R^{30}$ and $R^{31}$, taken together, may form ethylene or propylene, and $X^{16}$ is halogen).

Typical examples of compounds (13) used are compounds represented by the following formulae:

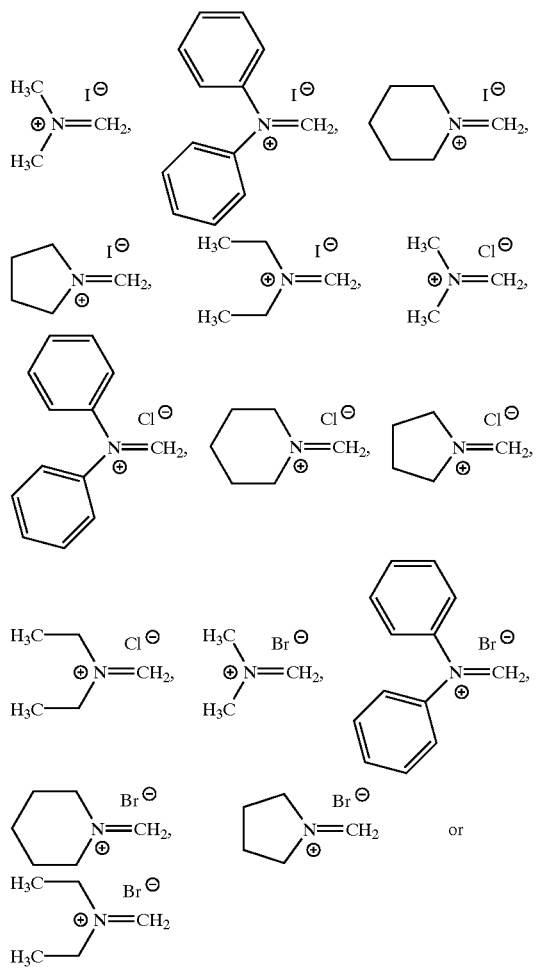

(14) A compound represented by the formula:

$$X^{17}\text{-}M^1$$

(wherein $X^{17}$ is halogen or $C_{1-4}$ alkoxy and $M^1$ is copper atom, silver atom or thallium atom).

Typical examples of compounds (14) used are monovalent metal compounds such as cuprous iodide, silver iodide, thallium chloride, thallium bromide, cuprous chloride, silver chloride, cuprous bromide and silver bromide.

(15) A compound represented by the formula:

$$X^{18}\text{-}M^2\text{-}X^{18}$$

(wherein $X^{18}$ is halogen or $C_{1-4}$ alkoxy, $M^2$ is zinc atom, mercury atom, nickel atom, manganese atom, palladium atom, iron atom or copper atom).

Typical examples of compounds (15) used are divalent metal compounds such as ferrous chloride, zinc chloride, mercuric chloride, cupric chloride, nickel chloride, palladium chloride, manganese chloride, manganese bromide, manganese iodide and manganese fluoride.

(16) A compound represented by the formula:

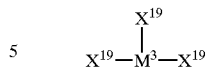

(wherein $X^{19}$ is halogen or $C_{1-4}$ alkoxy, $M^3$ is aluminum atom, titanium atom, gallium atom, indium atom, vanadium atom, ruthenium atom, cobalt atom, rare earth atom, scandium atom, yttrium atom or hafnium atom).

Typical examples of compound (16) used are trivalent metal compounds such as zirconium chloride, ferric chloride, ruthenium chloride, ruthenium bromide, ruthenium iodide, cobaltic chloride, scandium chloride, yttlium chloride, lanthanum chloride, ytterbium chloride, titanium chloride, aluminum chloride, vanadium chloride, vanadium fluoride, vanadium bromide and gallium chloride.

(17) A compound represented by the formula:

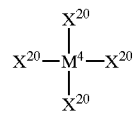

(wherein $X^{20}$ is halogen or $C_{1-4}$ alkoxy, $M^4$ is osmium atom, germanium atom, titanium atom, zirconium atom, vanadium atom, manganese atom, ruthenium atom or tin atom).

Typical examples of compounds (17) used are tetravalent metal compounds such as germanium chloride, germanium bromide, germanium fluoride, germanium iodide, germanium methoxide, germanium ethoxide, germanium isopropoxide, titanium chloride, titanium bromide, titanium iodide, titanium fluoride, titanium methoxide, titanium ethoxide, titanium isopropoxide, titanium butoxide, zirconium chloride, zirconium bromide, zirconium fluoride, zirconium iodide, zirconium methoxide, zirconium ethoxide, zirconium isopropoxide, zirconium butoxide, zirconium t-butoxide, vanadium chloride, vanadium bromide, vanadium iodide, tin chloride, tin bromide, tin fluoride and tin iodide.

(18) A compound represented by the formula:

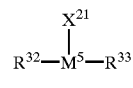

(wherein $R^{32}$ and $R^{33}$ are independently $C_{1-4}$ alkyl, $X^{21}$ is halogen or $C_{1-4}$ alkoxy, and $M^5$ is aluminum atom)

Typical examples of compounds (18) used are aluminum (III) compounds such as diethylaluminum chloride, diethylaluminum bromide, diethylaluminum ethoxide, diethylaluminum iodide, diethylaluminum iodide, diisoproylaluminum chloride, dimethylaluminum iodide, dimethylaluminum chloride, dimethylaluminum bromide and dimethylaluminum iodide.

(19) A compound of the formula:

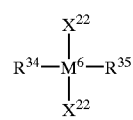

(wherein $R^{34}$ and $R^{35}$ are independently $C_{1-4}$ alkyl or phenyl, $X^{22}$ is halogen or $C_{1-4}$ alkoxy, and $M^6$ is tin atom).

Typical examples of compounds (19) used are tin (IV) compounds such as dibutyltin dichloride, dibutyltin dibromide, dibutyltin dimethoxide, dimethyltin dibromide, diphenyltin dibromide, dimethyltin dichloride and diphenyltin dichloride.

(20) A compound of the formula:

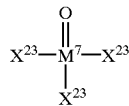

(20)

(wherein $X^{23}$ is halogen or $C_{1-4}$ alkoxy and $M^7$ is vanadium atom).

Typical examples of compounds (20) used are vanadium (V) compounds such as vanadium oxytrichloride, vanadium oxytrifluoride, vanadium oxytribromide, vanadium oxytriethoxide, vanadium oxytriisopropoxide, vanadium oxytributoxide and vanadium oxytri-t-butoxide.

(21) A compound of the formula:

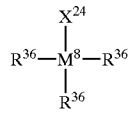

(21)

(wherein $X^{24}$ is trifluoromethanesulfonyloxy or halogen, $R^{36}$ is $C_{1-4}$ alkyl or phenyl, and $M^8$ is silicon atom)

Typical examples of compounds (21) used are silane derivatives such as chlorotrimethylsilane, chlorotriethylsilane, chlorotributylsilane, chlorotriisoproylsilane, chlorotriphenylsilane, bromotrimethylsilane, bromotriethylsilane, bromotributylsilane, bromotriisopropylsilane, bromotriphenylsilane, trifluoromethanesulfonyloxytrimethylsilane, trifluoromethanesulfonyloxytriethylsilane, trifluorosulfonyloxytributylsilane, trifluoromethanesulfonyloxytriisopropylsilane, and iodotrimethylsilane.

Among compounds (1) to (21) as described above, benzaldehyde, N,N-dimethylformamide or chlorotrimethylsilane is preferable as a compound having an electrophilic group. The substitution of the present invention is carried out first by reacting an exchange reagent of the present invention with a halogenated compound dissolved in an inert solvent. More specifically, the halogenated compound dissolved in an inert solvent is added below −5° C. over a period of about 15 minutes to one hour, preferably about 15 minutes to 30 minutes, and then the reaction is usually carried out at −10° C. for about one to two hours.

The inert solvent for dissolution of the halogenated compound can be any solvents used in halogen-metal exchange reaction with Grignard reagents and organolithium reagents. Such solvents include, for example, toluene, xylene, tetrahydrofuran, diethyl ether and dimethoxyethane, and a mixture thereof.

The halogenated compound dissolved in an inert solvent can be used usually in approximately 3 to 4 equivalents to the present reagent for exchange reaction.

Then, to the resultant reaction solution is added a compound with an electrophilic group usually below 0° C. over a period of about 5 to 10 minutes. The mixture is allowed to react at the same temperature for about 30 minutes to one hour.

The compound having an electrophilic group is used usually in approximately 1 to 3 equivalents, preferably to 1.2 to 2 equivalents, to the halogenated compound.

When the compound having an electrophilic group is, for example,

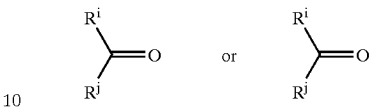

(wherein $R^i$ and $R^j$ are the same or different and are each an optionally substituted hydrocarbon group), the reaction product is treated with an acid. For example, an acid is added usually below 0° C. and the reaction is carried out at the same temperature for 10 minutes to 2 hours.

The above acid treatment is carried out, for example, at about 0° C. for 10 minutes to 2 hours using 1 to 10 equivalents of ammonium chloride, formic acid, trifluoroacetic acid, aqueous citric acid, aqueous acetic acid, hydrochloric acid or dilute sulfuric acid.

The thus obtained compounds by the exchange reaction as described above can be purified and isolated, if required, solely or in combination with the methods known per se in the art, such as chromatography on silica gel or adsorptive resin, liquid chromatography, thin layer chromatography, solvent extraction, and recrystallization/reprecipitation.

The present exchange reaction is concerned with an improved exchange of functional groups by means of halogen-metal exchange reaction with known Grignard reagents and/or organolithium compounds. Therefore, reaction conditions employed in the halogen-metal exchange reaction of Grinard reagents and/or organolithium reagents with electrophilic reagents, including purification of the reaction product except for reaction temperature, can be adopted as the reaction conditions for each step of the present invention.

The process of the present invention relates to a process for producing a compound wherein a halogen atom present in a halogenated compound is substituted with an electrophilic group, which comprises reacting (i) a halogenated compound having in the molecule at least one halogen atom or one double or triple bond to which is attached a halogen-substituted carbon atom, with (ii) an exchange reagent of the present invention, reacting the resultant product with (iii) a compound having an electrophilic group, and optionally hydrolyzing the resultant product.

The present process can be carried out according to the aforementioned substitution method of this invention.

When the aforementioned compound (V), compound (VI), compound (VII) and compound (VIII) are employed as the halogenated compound, the reaction products include, for example, (1) a compound represented by the formula:

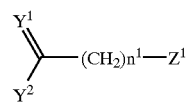

(wherein $Z^1$ is an electrophilic group and other symbols are each the same as defined above), (2) a compound represented by the formula:

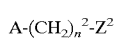

(wherein $Z^2$ is an electrophilic group and other symbols are each the same as defined above)

(3) a compound represented by the formula:

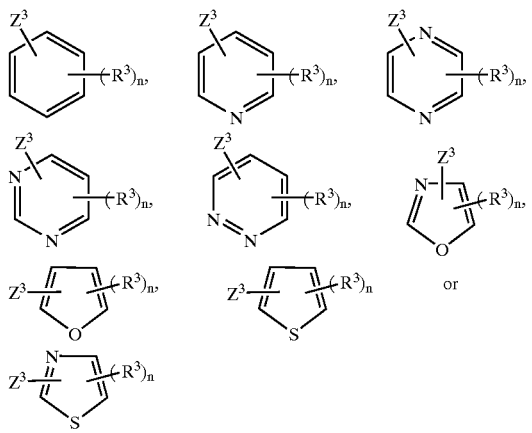

(wherein $Z^3$ is an electrophilic group and other symbols are each the same as defined above), and (4) a compound represented by the formula:

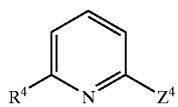

(wherein $Z^4$ is an electrophilic group and other symbols are each the same as defined above).

In the above formulae, the electrophilic groups represented by $Z^1$, $Z^2$, $Z^3$ and $Z^4$ are the same as those exemplified above for the compounds having an electrophilic group, among which the preferred electrophilic group represented by $Z^1$, $Z^2$, $Z^3$ and $Z^4$ is —C(=O)H.

The most preferred process of the present invention relates to a process for preparing 6-bromo-2-formylpyridine or a compound represented by the formula:

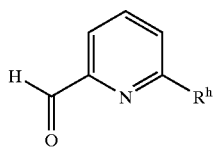

(wherein $R^h$ is amino protected by pivaloyl, benzyl, phthaloyl or t-butoxycarbonyl), which comprises reacting 2,6-dibromo-pyridine or a compound represented by the formula:

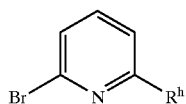

(wherein $R^h$ is amino protected by pivaloyl, benzyl, phthaloyl or t-butoxycarbonyl) with a mixture of n-butyl magnesium bromide and n-buityl lithium, or a reaction product from them, reacting the resultant product with N,N-dimethylformamide and hydrolyzing the resultant product with an acid.

Efficiency in the production of compounds whose halogen atom is substituted with an electrophilic group is remarkably enhanced by use of the present exchange reaction for functional groups, i.e. halogen-metal exchange reaction.

Namely, the exchange reaction for functional groups according to the present halogen-metal exchange reaction can be carried out at about −10° C. to room temperature, different from extreme low temperature conditions usually employed, in equimolar amount of reactants to a halogenated compound, so that cooling equipments for extreme low temperature are not required and the amount of the reactants can be reduced, which results in enhancement of efficiency for industrial production.

The compounds obtained by the present substitution reaction or the production method can be used as a synthetic intermediate for pharmaceuticals or agrochemicals.

More specifically, 6-bromo-2-formylpyridine prepared by the working examples hereinafter described is useful as an intermediates for (i) fluorine-containing 1,4-disubstituted-piperidine derivatives which possess highly selective muscarine M3 receptor antagonist activity remarkably useful for treatment or prophylaxis of various diseases in respiratory tract, urinary tract or digestive organ, as disclosed in WO98/05641, (ii) 1-pyridyl naphthalene derivatives which are phosphodiesterase-4 inhibitors useful for treatment of asthma, as disclosed in Journal of Medicinal Chemistry, Vol. 42, pages 1088–1099 (1999) by Tatsuo Ukita, et al., and (iii) 2,6-disubstituted-pyridine derivatives which are leukotriene B4 receptor antagonists useful as anti-inflammatory agents, as disclosed in Tetrahedron Letters Vol. 29, pages 143–146 (1999) by J. Morris, et al, and WO88/05045. 5-Bromo-3-formylpyridine is a useful synthetic intermediate for azabicycloaminobenzoic acid derivatives which show integrin antagonistic activity and are useful for treatment of tumour metastasis, solid tumour, humoral hypercalcemia as disclosed in WO97/08145. 4-Bromo-2-fluorobenzaldehyde can be an intermediate for the synthesis of benzopyran derivatives possessing LTB4 antagonistic activity useful for treatment of chronic rheumatoid arthritis, osteoarthritis, eczema, cerebral apoplexy, autoimmune disease or inflammatory diseases including asthma.

THE BEST MODE FOR CARRYING OUT THE INVENTION

The present invention is hereinafter described in more detail by means of working examples and reference examples, and these examples are not intended to be limiting to the scope of the invention in any respect.

WORKING EXAMPLE 1

Production of 6-bromo-2-formylpyridine

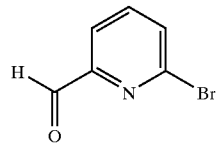

n-Butyllithium (337 mmol) in 1.52M hexane solution (222 mL) was dissolved in toluene (500 mL) cooled at −10° C., and n-butylmagnesium chloride (169 mmol) in 2.00M tetrahydrofuran solution (84.5 ml) was added dropwise below −10° C. over a period of 25 minutes. After stirring at −10° C. for one hour, 2,6-dibromopyridine (100 g, 422 mmol) in toluene (1000 mL) was added dropwise to the mixture at an inside temperature of −10° C. to −6° C. over one hour. The mixture was further stirred at −10° C. for 1.5 hours and then N,N-dimethylformamide (65 mL, 840 mmol) was added dropwise below −2° C. over 20 minutes. After further stirring at 0° C. for one hour, 10% aqueous acetic acid solution (750 mL) was added. The mixture was stirred under ice-cooling and the organic phase was separated. The extract was washed with saturated aqueous sodium chloride (25 mL), dried over anhydrous sodium sulfate and concentrated to give 6-bromo-2-formylpyridine (74.68 g, 98% purity, 95% yield) as a pale yellowish solid.

$^1$H-NMR (270 MHz, CDCl$_3$, δ ppm): 7.71–7.80 (m, 2H), 7.93 (m, 1H), 10.01 (s, 2H).

WORKING EXAMPLE 2

Production of 1-(6-bromopyridin-2-yl)benzyl alcohol

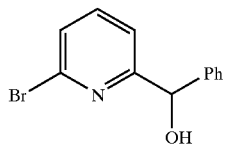

n-Butylmagnesium chloride (3.49 mmol) in 2.05M tetrahydrofuran solution (1.70 mL) was added to ice-cooled n-butyllithium (7.03 mmol) in 1.45M hexane solution (4.85 mL) ("Hexanes", Product of Wako Pure and Chemical Industries, Ltd. The solvent was used in the same way in the working examples hereinafter described). The mixture was stirred at 0° C. for 15 minutes, and then cooled to −10° C. to give a suspension. 2,6-Dibromopyridine (2.37 g, 10.0 mmol) in toluene (25 mL) was added to the suspension below −5° C. over a period of 10 minutes or more. The mixture was stirred at −10° C. for 2 hours, and then benzaldehyde (1.35 ml, 13.3 mmol) was added. After stirring at 0° C. for one hour, 1M acetic acid solution (15 mL) was added. The organic phase was separated, and the aqueous phase was extracted twice with ethyl acetate (10 mL). The organic extracts were combined, washed with an aqueous saturated solution (10 mL) of sodium chloride, dried over magnesium sulfate and concentrated under reduced pressure to remove the solvent. The resultant residue was purified by flash column chromatography on silica gel in a developing solvent system of hexane-ethyl acetate (15:1, v/v) to give the title compound (2.56 g) in 97% yield as a pale yellowish viscous oil.

$^1$H-NMR (CDCl$_3$) δ ppm: 4.41 (0.9H, d, J=4.5 Hz), 4.71 (0.1H, br), 5.76 (1H, d, J=4.5 Hz), 7.14 (1H, d, J=7.7 Hz), 7.28–7.41 (6H, m), 7.49 (1H, t, J=7.7 Hz).

WORKING EXAMPLE 3

Production of 6-bromo-2-cyanopyridine

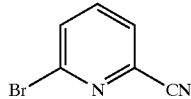

n-Butylmagnesium chloride (3.49 mmol) in 2.05M tetrahydrofuran solution (1.70 mL) was added to ice-cooled n-butyllithium (7.03 mmol) in 1.45M hexane (4.85 mL). The mixture was stirred at 0° C. for 15 minutes, and cooled to −10° C. to give a suspension. 2,6-Dibromopyridine (2.37 g, 10 mmol) in toluene (25 mL) was added to the suspension below −5° C. over a period of 10 minutes or more. The mixture was stirred at −10° C. for 3 hours, and p-toluenesulfonyl cyanide (2.48 g, 13.3 mmol) was added. After the mixture was stirred at 0° C. for 30 minutes, an aqueous solution (15 mL) of 1M acetic acid was added thereto. The reaction mixture was extracted twice with ethyl acetate (50 mL). The organic extracts combined were washed with an aqueous saturated solution (15 mL) of sodium chloride, dried over magnesium sulfate, and purified by flash column chromatography on silica gel in a developing solvent system of hexane-ethyl acetate (10:1, v/v) to give the title compound (942 mg, about 51% yield) as orange powder.

WORKING EXAMPLE 4

Production of (6-bromopyridin-2-yl)trimethylsilane

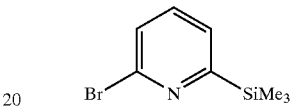

n-Butylmagnesium chloride (4.00 mmol) in 2.00M tetrahydrofuran solution (2.00 mL) was added to ice-cooled n-butyllithium (8.06 mmol) in 1.55M hexane (5.20 mL). The mixture was stirred at 0° C. for 15 minutes, and 2,6-dibromopyridine (2.37 g, 10.0 mmol) in toluene (25 mL) was added thereto below 10° C. over a period of 10 minutes or more. The resultant suspension was stirred at 0° C. for one hour, and chlorotrimethylsilane (13 mmol, 1.65 mL)) was added thereto. After the mixture was stirred at 0° C. for one hour and at room temperature for 1.5 hours, an aqueous solution (20 mL) of 1M acetic acid was added thereto. The reaction mixture was extracted twice with ethyl acetate (50 mL). The organic phase was separated, washed with water (10 mL), dried over magnesium sulfate, and concentrated under reduced pressure to give a residue. The residue was purified by flash column chromatography on silica gel in a developing solvent system of hexane-ethyl acetate (20:1, v/v) to give the title compound (881 mg, about 38% yield) as colorless powder.

$^1$H-NMR (CDCl$_3$) δ ppm: 0.32 (9H, s), 7.37 (1H, dd, J=3.2, 6.0 Hz), 7.42 (1H, dd, J=3.0, 3.2 Hz), 7.43 (1H, d, J=3.0, 3.8 Hz).

WORKING EXAMPLE 5

Production of 6-bromo-3-formylpyridine

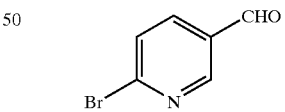

n-Butylmagnesium chloride (4.00 mmol) in 2.00M tetrahydrofuran solution (2.00 mL) was added to ice-cooled n-butyllithium (8.06 mmol) in 1.55M hexane (20 mL). The mixture was stirred at 0° C. for 15 minutes to give a suspension. The suspension was added to a mixture of toluene (15 mL) and tetrahydrofuran (10 mL) containing 2,5-dibromopyridine (2.37 g, 10.0 mmol) over a period of 10 minutes or more while keeping the temperature below −5° C. to give a dark orange solution. The solution was stirred at 0° C. for 1.25 hours and then at 20° C. for one hour. The solution was cooled to 0° C., and N,N-dimethylformamide (1.0 mL, 13 mmol) was added thereto. After the mixture was stirred at 0° C. for 30 minutes, 1M aqueous acetic acid solution (20 mL) was added. The organic phase was separated, and the aqueous phase was extracted twice with ethyl acetate (10 mL). The organic phases were combined, washed with saturated aqueous sodium chloride (15 mL), dried over magnesium sulfate and concentrated under reduced pressure to remove the solvent. The resultant residue was purified by flash column chromatography on silica gel in a developing solvent system of hexane-ethyl acetate (20:1, v/v) to give the title compound (1.229 g, 66% yield) as a colorless solid.

$^1$H-NMR (CDCl$_3$) δ ppm: 7.69 (1H, d, J=8.4 Hz), 8.02 (1H, dd, J=2.4, 8.4 Hz), 8.84 (1H, d, J=2.4 Hz), 10.10 (1H, s).

WORKING EXAMPLE 6

Production of 5-bromo-3-formylpyridine

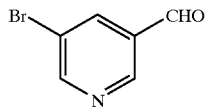

n-Butylmagnesium chloride (4.00 mmol) in 2.00M tetrahydrofuran solution (2.00 mL) was added to ice-cooled n-butyllithium (8.06 mmol) in 1.55M hexane (5.20 mL). The mixture was stirred at 0° C. for 15 minutes to give a suspension. The suspension was added to a mixture of toluene (15 mL) and tetrahydrofuran (10 mL) containing 2,5-dibromo-pyridine (2.37 g, 10.0 mmol) over a period of 10 minutes or more while keeping the temperature below 5° C. to give an orange solution. The solution was stirred at 0° C. for one hour, and N,N-dimethylformamide (1.0 mL, 13 mmol)was added thereto. The resultant suspension was stirred at room temperature for 30 minutes, and tetrahydrofuran (10 mL) was added, followed by further stirring at room temperature for 30 minutes. After addition of 1M aqueous acetic acid (20 mL) to the suspension, the organic phase was separated, and the aqueous phase was extracted with toluene (20 mL). The organic phase and the toluene extract were combined, washed with an aqueous sodium chloride saturated solution (15 mL), dried over magnesium sulfate and concentrated under reduced pressure to remove the solvent. The resultant residue was purified by flash column chromatography on silica gel in a developing solvent system of hexane-ethyl acetate (10:1, v/v) to give the title compound (1.062 g, 57% yield) as a colorless solid.

$^1$H-NMR (CDCl$_3$) δ ppm: 8.31 (1H, dd, J=1.5, 2.2 Hz), 8.92 (1H, d, J=2.2 Hz), 9.00 (1H, d, J=1.5 Hz), 10.09 (1H, s).

WORKING EXAMPLE 7

Production of 1-(5-bromopyridin-3-yl)benzyl alcohol

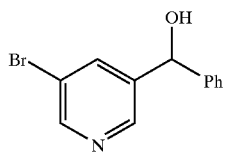

n-Butylmagnesium chloride (3.49 mmol) in 2.05M tetrahydrofuran solution (1.70 mL) was added to ice-cooled n-butyllithium (6.99 mmol) in 1.52M hexane (4.60 mL). The mixture was stirred at 0° C. for 15 minutes to give a suspension. The suspension was added to a tetrahydrofuran solution (25 mL) containing 3,5-dibromopyridine (2.37 g, 10.0 mmol) over a period of 10 minutes or more, while keeping the temperature below −5° C., to give an orange suspension. The suspension was stirred at −10° C. for one hour, and benzaldehyde (1.35 mL, 13.3 mmol) was added thereto. The resultant mixture was stirred at 0° C. for 30 minutes, and then 1M acetic acid solution (15 mL) was added. The reaction mixture was extracted twice with ethyl acetate (20 mL). The organic extracts were combined, washed with saturated aqueous sodium chloride (10 mL), dried over magnesium sulfate and was purified by flash column chromatography on silica gel in a developing solvent system of hexane-ethyl acetate (5:1, v/v) to give the title compound (1.647 g, 59% yield) as a colorless oil.

$^1$H-NMR (CDCl$_3$) δ ppm: 2.57 (1H, br), 5.85 (1H, s), 7.30–7.41 (5H, m), 7.89 (1H, dt, J=0.7, 2.2), 8.51 (1H, s), 8.55 (1H, s).

WORKING EXAMPLE 8

Production of 4-bromobenzaldehyde

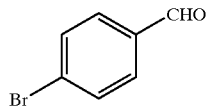

n-Butylmagnesium chloride (4.00 mmol) in 2.00M tetrahydrofuran solution (2.00 mL) was added to ice-cooled n-butyllithium (8.06 mmol) in 1.55M hexane (5.20 mL). The mixture was stirred at 0° C. for 15 minutes to give a suspension. To the suspension was added dropwise a toluene solution (25 mL) containing 1,4-dibromobenzene (2.36 g, 10 mmol) over a period of 15 minutes, while keeping the temperature below 5° C., to give a white suspension. After the suspension was stirred at 0° C. for 5 hours, N,N-dimethylformamide (1.0 mL, 13 mmol) was added thereto. The resultant mixture was stirred at 0° C. for 30 minutes, and 10% acetic acid solution (20 mL) was added. The organic phase was separated and the aqueous phase was extracted with toluene (20 mL). The organic layers were combined, washed with water (20 mL), and dried over magnesium sulfate. Toluene was added to the solution to a volume of 100 mL. The solution (98 ml) was purified by flash column chromatography on silica gel in a developing solvent system of hexane-ethyl acetate (30:1, v/v) to give the title compound (1.507 g, 81% yield) as a colorless crystalline solid.

$^1$H-NMR (CDCl$_3$) δ ppm: 7.67–7.77 (4H, AB-like m), 9.98 (1H, s).

WORKING EXAMPLE 9

Production of 3-bromobenzaldehyde

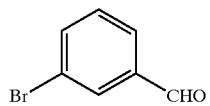

n-Butylmagnesium chloride (4.00 mmol) in 2.00M tetrahydrofuran solution (2.00 mL) was added to ice-cooled n-butyllithium (8.06 mmol) in 1.55M hexane (5.20 mL). The mixture was stirred at 0° C. for 15 minutes to give a suspension. To the suspension was added dropwise a toluene solution (25 mL) containing 1,3-dibromobenzene (2.36 g, 10.0 mmol), while keeping the temperature below 5° C., over a period of 15 minutes, thereby to give a suspension. The suspension was stirred at 0° C. for 5 hours, and then N,N-dimethylformamide (1.0 mL, 13 mmol) was added thereto. The resultant mixture was stirred at 0° C. for 30 minutes, and 10% aqueous acetic acid (20 mL) was added. The reaction mixture was extracted twice with toluene (20 mL). The organic extracts were combined, washed with water (20 mL), and dried over magnesium sulfate. Toluene was added to the solution to a volume of 85 mL. The solution (83 ml) was purified by flash column chromatography on silica gel in a developing solvent system of hexane-ethyl acetate (25:1, v/v) to give the title compound (1.446 g, 78% yield) as a pale yellowish crystalline solid.

$^1$H-NMR (CDCl$_3$) δ ppm: 7.43 (1H, t, J=2.0), 7.76 (1H, ddd, J=1.3, 2.0, 7.9), 7.81 (dt, J=1.3, 7.9), 8.02 (1H, t, J=2.0), 9.97 (1H, s).

WORKING EXAMPLE 10

Production of 4-bromo-2-fluorobenzaldehyde

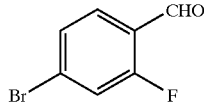

n-Butylmagnesium chloride (3.49 mmol) in 2.05M tetrahydrofuran solution (1.70 mL) was added to ice-cooled n-butyllithium (8.06 mmol) in 1.45M hexane (4.85 mL). The mixture was stirred at 0° C. for 15 minutes to give a suspension. To the suspension was added dropwise a toluene solution (25 mL) containing ice-cooled 1,4-dibromo-2-fluorobenzene (2.54 g, 10.0 mmol) over a period of 10 minutes, while keeping the temperature below 5° C. The resultant yellowish suspension was stirred at 0° C. for one hour, and N,N-dimethylformamide (1.0 mL, 13 mmol) was added thereto. The mixture was stirred at 0° C. for 30 minutes, and 1M aqueous acetic acid solution (15 mL) was added. The reaction mixture was extracted twice with ethyl acetate (15 mL). The organic extracts were combined, and 20% aqueous sodium hydrogen sulfite solution (5 mL) was added at room temperature. The mixture was stirred vigorously at room temperature for one hour. The aqueous phase was separated, washed with ethyl acetate (15 mL), adjusted to pH 10 with 6N sodium hydroxide solution, and extracted twice with ethyl acetate (25 ml). The organic extracts were combined, washed successively with aqueous ammonium chloride saturated solution (10 mL) and saturated aqueous sodium chloride (10 mL), dried over magnesium sulfate, and concentrated to dryness under reduced pressure to give the title compound (1.666 g, 82% yield) as an almost colorless crystalline solid.

$^1$H-NMR (CDCl$_3$) δ ppm: 7.40 (1H, dd, J=1.7, 9.7), 7.45 (1H, dddd, J=1.7, 1.7, 1.7, 8.3), 7.75 (1H, dd, J=7.4, 8.3), 10.31 (1H, s).

WORKING EXAMPLE 11

Production of 5-bromo-2-thiophenecarboxyaldehyde

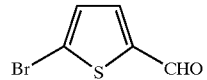

n-Butylmagnesium chloride (3.50 mmol) in 2.01M tetrahydrofuran solution (1.74 mL) was added to ice-cooled n-butyllithium (7.00 mmol) in 1.61M hexane (4.35 mL). The mixture was stirred at 0° C. for 15 minutes to give a suspension. To the suspension was added dropwise a toluene solution (25 mL) containing 2, 5-dibromothiophene (2.55 g, content 95 w/w %, 10.0 mmol) over a period of 10 minutes, while keeping the temperature below −5° C. The resultant pale yellowish suspension was stirred at −10° C. for 3 hours, and N,N-dimethylformamide (1.0 mL, 13 mmol) was added. The mixture was stirred at 0° C. for 30 minutes, and 1N aqueous acetic acid solution (15 mL) was added. The reaction mixture was extracted twice with ethyl acetate (15 mL). The organic extracts thus obtained were combined, washed with water (10 mL), dried over magnesium sulfate, and concentrated under reduced pressure to remove the solvent. The resultant residue was purified by flash column chromatography on silica gel in a developing solvent system of hexane-ethyl acetate (20:1, v/v) to give the title compound (1.387 g, 73% yield) as a yellow oil.

$^1$H-NMR (CDCl$_3$) δ ppm: 7.20 (1H, d, J=4.0), 7.52 (1H, d, J=4.0), 9.78 (1H, s).

REFERENCE EXAMPLE

Production of 6-bromo-2-formylpyridine

A solution (650 mL) of 2,6-dibromopyridine (100 g, 422 mmol) in tetrahydrofuran was added dropwise to a tetrahydrofuran solution (250 mL) of butyllithium (as 1.57M hexane solution 282 mL, 435 mmol) over a period of 43 minutes, while keeping the temperature below −70° C. The mixture was stirred at −73° C. for 20 minutes, and N,N-dimethylformamide (98 mL, 1266 mmol) was added dropwise over a period of 25 minutes while keeping the temperature below −70° C. After further stirring for 20 minutes, the reaction solution was analyzed to indicate that physicochemical data of the product was identical to those as reported in the known literature, i.e. Journal of Inorganic Chemistry, Vol. 10, pages 2472–2478 (1971) by J. E. Parks, et al., and identified as 6-bromo-2-formylpyridine.

INDUSTRIAL APPLICABILITY

By use of the present reagents for exchange reaction for functional groups, a halogen atom in halogenated compounds can be efficiently substituted with an electrophilic group, and synthetic intermediates commonly used in the field of chemical industries, agrochemicals and pharmaceuticals can be prepared more efficiently.

What is claimed is:

1. A process for exchanging a halogen atom present in a halogenated compound for an electrophilic group, which comprises:

reacting (i) (1) a halogenated compound represented by the formula:

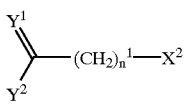 (V)

wherein $Y^1$ is a divalent organic residue, $Y^2$ is a monovalent organic residue, or $Y^1$ and $Y^2$, when taken together, represent a trivalent organic residue, $X^2$ is a halogen atom, and $n^1$ is 0 or 1, or (2) a halogenated compound represented by the formula:

A-(CH$_2$)n$^2$—X$^3$ (VI)

wherein A is an optionally substituted aromatic ring, $n^2$ is 0 or 1 and $X^3$ is a halogen atom, with (ii) an exchange reagent which comprises a mixture of (A)
(1) a magnesium compound represented by the formula:

R$^1$—Mg—X$^1$ (I)

wherein $R^1$ is a halogen atom or an optionally substituted hydrocarbon residue, and $X^1$ is a halogen atom or (2) a member selected from the group consisting of diethylmagnesium, dipropylmagnesium, diisopropylmagnesium, di-n-butylmagnesium, di-sec-butylmagnesium, di-tert-butylmagnesium, diphenylmagnesium, divinylmagnesium, diallylmagnesium, di(2-furyl)magnesium, di(3-furyl)magnesium, di(2-thienyl)magnesium, di(3-thienyl)magnesium and dibenzylmagnesium and (B) an organolithium compound represented by the formula:

R$^2$—Li (II)

wherein $R^2$ is an optionally substituted hydrocarbon residue, or a reaction product from (A) and (B), reacting the resultant product with (iii) a compound having an electrophilic group, and optionally treating the resultant product with an acid.

2. A process for exchanging a halogen atom present in a halogenated compound for an electrophilic group, which comprises:

reacting (i) a halogenated compound represented by the formula:

(VII)

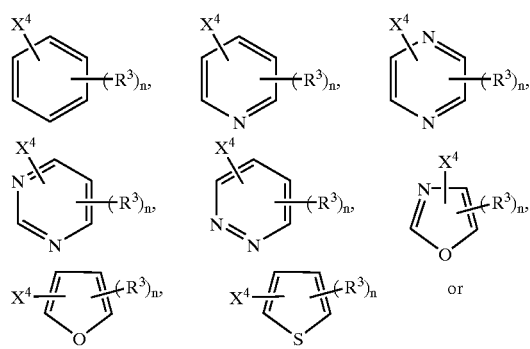

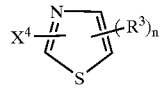
-continued wherein $X^4$ is a halogen atom, $R^3$ is a hydrogen atom, a protected amino group, an optionally substituted hydrocarbon group, an optionally substituted hydrocarbon-oxy group or a halogen atom, and n is 1 or 2, with (ii) an exchange reagent which comprises a mixture of (A)
(1) a magnesium compound represented by the formula:

R$^1$—Mg—X$^1$ (I)

wherein $R^1$ is a halogen atom or an optionally substituted hydrocarbon residue, and $X^1$ is a halogen atom or (2) a member selected from the group consisting of diethylmagnesium, dipropylmagnesium, diisopropylmagnesium, di-n-butylmagnesium, di-sec-butylmagnesium, di-tert-butylmagnesium, diphenylmagnesium, divinylmagnesium, diallylmagnesium, di(2-furyl)magnesium, di(3-furyl)magnesium, di(2-thienyl)magnesium, di(3-thienyl)magnesium and dibenzylmagnesium and (B) an organolithium compound represented by the formula:

R$^2$—Li (II)

wherein $R^2$ is an optionally substituted hydrocarbon residue, or a reaction product from (A) and (B), reacting the resultant product with (iii) a compound having an electrophilic group, and optionally treating the resultant product with an acid.

3. A process for exchanging a halogen atom present in a halogenated compound for an electrophilic group, which comprises:

reacting (i) a halogenated compound represented by the formula:

(VIII)

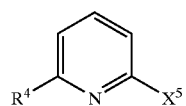

wherein $R^4$ is a hydrogen atom, a protected amino group, an optionally substituted hydrocarbon group, an optionally substituted hydrocarbon-oxy group or a halogen atom, and $X^5$ is a halogen atom, with (ii) an exchange reagent which comprises a mixture of (A)
(1) a magnesium compound represented by the formula:

R$^1$—Mg—X$^1$ (I)

wherein $R^1$ is a halogen atom or an optionally substituted hydrocarbon residue, and $X^1$ is a halogen atom or (2) a member selected from the group consisting of diethylmagnesium, dipropylmagnesium, diisopropylmagnesium, di-n-butylmagnesium, di-sec-butylmagnesium, di-tert-butylmagnesium, diphenylmagnesium, divinylmagnesium, diallylmagnesium, di(2-furyl)magnesium, di(3-furyl)magnesium, di(2-thienyl)magnesium, di(3-thienyl)magnesium and dibenzylmagnesium and (B) an organolithium compound represented by the formula:

R²—Li (II)

wherein R² is an optionally substituted hydrocarbon residue, or a reaction product from (A) and (B), reacting the resultant product with (iii) a compound having an electrophilic group, and optionally treating the resultant product with an acid.

4. The process according to any one of claims 1 to 3, wherein the compound having an electrophilic group is benzaldehyde, chlorotrimethylsilane or N,N-dimethylformamide.

5. The process according to any one of claims 1 to 3, wherein the magnesium compound represented by the formula (I) is n-butylmagnesium bromide or n-butylmagnesium chloride, and the organolithium compound represented by the formula (II) is n-butyllithium.

6. The process according to any one of claims 1 to 3, wherein the reaction product from (A) and (B) is
(1) a compound represented by the formula:

(R$^a$R$^b$R$^c$Mg)$^-$.Li$^+$ (III)

wherein R$^a$, R$^b$ and R$^c$ are the same or different and are each an optionally substituted hydrocarbon residue, or
(2) a compound represented by the formula:

(R$^d$R$^e$R$^f$R$^g$Mg)$^{2-}$.2Li$^+$ (IV)

wherein R$^d$, R$^e$, R$^f$ and R$^g$ are the same or different and are each an optionally substituted hydrocarbon residue.

7. The process according to claim 6, wherein R$^a$, R$^b$ and R$^c$ are each n-butyl group.

8. The process according to claim 6, wherein R$^d$, R$^e$, R$^f$ and R$^g$ are each n-butyl group.

9. The process according to claim 6, wherein the compound represented by the formula (III) is tri-n-butylmagnesium lithium, and the compound represented by the formula (IV) is tetra-n-butylmagnesium dilithium.

10. The process according to any one of claims 1 to 3, which comprises reacting, as the halogenated compound, 2-6-dibromopyridine or a compound represented by the formula:

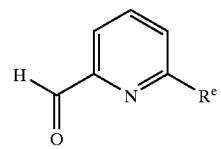

wherein R$^e$ is a protected amino group, with, as the exchange reagent, a mixture of n-butylmagnesium chloride and n-butyllithium, or a reaction product thereof, reacting the product with N,N-dimethylformamide, and treating the product with an acid, to obtain 6-bromo-2-formylpyridine or a compound represented by the formula:

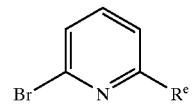

wherein R$^e$ is a protected amino group.

11. The process according to any one of claims 1 to 3, wherein the reagent (A) is di-n-butylmagnesium.

* * * * *